(12) United States Patent
Marsh et al.

(10) Patent No.: US 9,211,065 B2
(45) Date of Patent: Dec. 15, 2015

(54) DISTRIBUTED CONTROL OF MEDICAL DEVICES TO AVOID EFFECTS OF INTERFERENCE

(71) Applicant: QUALCOMM Incorporated, San Diego, CA (US)

(72) Inventors: Gene Wesley Marsh, Encinitas, CA (US); Rahul Anand, San Diego, CA (US); Brad L. Vaughn, San Diego, CA (US); Jen Mei Chen, San Diego, CA (US); Tao Chen, La Jolla, CA (US); Jin Guo, San Diego, CA (US); Navrina B. Singh, San Diego, CA (US); Joseph Doroba, San Diego, CA (US); Jiang Zhang, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 281 days.

(21) Appl. No.: 13/654,368

(22) Filed: Oct. 17, 2012

(65) Prior Publication Data

US 2013/0102253 A1 Apr. 25, 2013

Related U.S. Application Data

(60) Provisional application No. 61/549,076, filed on Oct. 19, 2011.

(51) Int. Cl.
*H04B 7/00* (2006.01)
*A61B 5/00* (2006.01)
(Continued)

(52) U.S. Cl.
CPC .............. *A61B 5/0015* (2013.01); *H04W 4/008* (2013.01); *H04W 76/025* (2013.01); *H04W 88/06* (2013.01); *H04W 88/10* (2013.01); *H04W 48/18* (2013.01)

(58) Field of Classification Search
USPC ...................... 455/404.1–404.2, 414.1–414.3, 455/456.1–456.6, 457, 41.1–41.2, 455/556.1–556.2, 517, 521; 340/539.1, 340/539.11–539.19, 539.2, 539.21–539.29; 607/60, 62, 63
See application file for complete search history.

(56) References Cited

U.S. PATENT DOCUMENTS

| 6,263,280 B1 * | 7/2001 | Stingone, Jr. ................. 701/485 |
| 6,544,171 B2 * | 4/2003 | Beetz et al. .................... 600/300 |

(Continued)

FOREIGN PATENT DOCUMENTS

| EP | 1551140 A1 | 7/2005 |
| EP | 1793531 A1 | 6/2007 |

(Continued)

OTHER PUBLICATIONS

Cho, et al., "Optimal beacon scheduling mechanisms using cluster identifier for healthcare application," Expert Systems with Applications, pp. 5071-5080, vol. 36, Issue 3, 2009.

(Continued)

*Primary Examiner* — Tuan A Tran
(74) *Attorney, Agent, or Firm* — Joseph Hanasz (57) ABSTRACT

Certain aspects of the present disclosure provide techniques and apparatus for transmitting relatively more critical information between devices using a first wireless technology and transmitting relatively less critical information using a second wireless technology more susceptible to interference than the first wireless technology. One example method generally includes performing an association with a second apparatus via a first wireless technology, wherein the first wireless technology requires proximity between the first and second apparatuses; communicating first information with the second apparatus via the first wireless technology, a second wireless technology, or a combination of both the first and second wireless technologies, while the first and second apparatuses are still in proximity; and communicating second information with the second apparatus via the second wireless technology.

37 Claims, 4 Drawing Sheets

(51) Int. Cl.
*H04W 4/00* (2009.01)
*H04W 88/06* (2009.01)
*H04W 88/10* (2009.01)
*H04W 76/02* (2009.01)
*H04W 48/18* (2009.01)

(56) References Cited

U.S. PATENT DOCUMENTS

| | | | |
|---|---|---|---|
| 6,636,873 B1 | 10/2003 | Merchant et al. | |
| 6,792,396 B2* | 9/2004 | Inda et al. | 702/188 |
| 6,847,892 B2* | 1/2005 | Zhou et al. | 701/408 |
| 7,300,418 B2 | 11/2007 | Zaleski | |
| 7,406,105 B2 | 7/2008 | DelMain et al. | |
| 7,825,794 B2* | 11/2010 | Janetis et al. | 340/539.13 |
| 7,978,062 B2 | 7/2011 | Lalonde et al. | |
| 7,978,063 B2* | 7/2011 | Baldus et al. | 340/539.12 |
| 8,082,160 B2 | 12/2011 | Collins, Jr. et al. | |
| 8,112,293 B2* | 2/2012 | Howell et al. | 705/3 |
| 8,149,131 B2 | 4/2012 | Blomquist | |
| 8,156,439 B2 | 4/2012 | Booth | |
| 8,300,560 B2* | 10/2012 | Nowlan et al. | 370/270 |
| 8,437,694 B2* | 5/2013 | Granqvist et al. | 455/41.1 |
| 8,594,573 B2* | 11/2013 | Miettinen et al. | 455/41.2 |
| 2001/0026240 A1* | 10/2001 | Neher | 342/357.07 |
| 2003/0125017 A1* | 7/2003 | Greene et al. | 455/414 |
| 2004/0162035 A1* | 8/2004 | Petersen et al. | 455/90.1 |
| 2005/0055244 A1 | 3/2005 | Mullan et al. | |
| 2006/0101451 A1 | 5/2006 | Fong | |
| 2007/0038823 A1 | 2/2007 | Banks | |
| 2007/0176790 A1 | 8/2007 | Klabunde et al. | |
| 2007/0190939 A1 | 8/2007 | Abel | |
| 2007/0233521 A1 | 10/2007 | Wehba et al. | |
| 2007/0254593 A1 | 11/2007 | Jollota et al. | |
| 2008/0228832 A1 | 9/2008 | Wetmore et al. | |
| 2010/0298718 A1 | 11/2010 | Gilham et al. | |
| 2010/0315225 A1 | 12/2010 | Teague | |
| 2011/0054337 A1 | 3/2011 | Lupano et al. | |
| 2011/0149759 A1 | 6/2011 | Jollota | |
| 2012/0003933 A1 | 1/2012 | Baker et al. | |
| 2012/0106397 A1 | 5/2012 | Abedi | |
| 2013/0102963 A1 | 4/2013 | Marsh et al. | |

FOREIGN PATENT DOCUMENTS

| | | |
|---|---|---|
| EP | 2107837 A1 | 10/2009 |
| GB | 2475157 A | 5/2011 |
| JP | 2011097189 A | 5/2011 |
| WO | 2009058494 A1 | 5/2009 |

OTHER PUBLICATIONS

McCann, "FCC gives green light to wireless medical devices," Healthcare IT News, http://www.healthcareitnews.com, pp. 1-2, May 24, 2012.

International Search Report and Written Opinion—PCT/US2012/061174—ISA/EPO—Feb. 8, 2013.

Milojicic D., et al., "Process Migration", Feb. 1, 1999, pp. 0-48, XP055012410, Palo Alto Retrieved from the Internet: URL:http://www.hpl.hp.com/techreports/1999/HPL-1999-21.pdf.

* cited by examiner

DISTRIBUTED CONTROL OF MEDICAL DEVICES TO AVOID EFFECTS OF INTERFERENCE

CROSS-REFERENCE TO RELATED APPLICATIONS

This application claims benefit of U.S. Provisional Patent Application Ser. No. 61/549,076, filed Oct. 19, 2011, which is herein incorporated by reference.

BACKGROUND

1. Field

Certain aspects of the present disclosure generally relate to wireless communications and, more particularly, to transmitting critical information between devices using a wireless technology that is less susceptible to interference.

2. Background

As various wireless communication techniques have evolved, many have achieved not only increased data rates, but also increased signal-to-interference-plus-noise ratio (SINR), quality of service (QoS), and reliability. With this increased reliability, certain wireless communication techniques are being considered for use in an ever-expanding number of new applications.

SUMMARY

Certain aspects of the present disclosure generally relate to transmitting more critical information between devices using a first wireless technology and transmitting relatively less critical information using a second wireless technology, wherein the first wireless technology is less susceptible to interference than the second wireless technology.

Certain aspects of the present disclosure provide a method for wireless communications by a first apparatus. The method generally includes performing an association with a second apparatus via a first wireless technology, wherein the first wireless technology requires proximity between the first and second apparatuses; communicating first information with the second apparatus via the first wireless technology, a second wireless technology, or a combination of both the first and second wireless technologies, while the first and second apparatuses are still in proximity; and communicating second information with the second apparatus via the second wireless technology.

Certain aspects of the present disclosure provide a first apparatus for wireless communications. The first apparatus generally includes a processing system configured to perform an association with a second apparatus via a first wireless technology, wherein the first wireless technology requires proximity between the first and second apparatuses; to communicate first information with the second apparatus via the first wireless technology, a second wireless technology, or a combination of both the first and second wireless technologies, while the first and second apparatuses are still in proximity; and to communicate second information with the second apparatus via the second wireless technology.

Certain aspects of the present disclosure provide a first apparatus for wireless communications. The first apparatus generally includes means for performing an association with a second apparatus via a first wireless technology, wherein the first wireless technology requires proximity between the first and second apparatuses; means for communicating first information with the second apparatus via the first wireless technology, a second wireless technology, or a combination of both the first and second wireless technologies, while the first and second apparatuses are still in proximity; and means for communicating second information with the second apparatus via the second wireless technology.

Certain aspects of the present disclosure provide a computer-program product for wireless communications by a first apparatus. The computer-program product generally includes a computer-readable medium having instructions executable to perform an association with a second apparatus via a first wireless technology, wherein the first wireless technology requires proximity between the first and second apparatuses; to communicate first information with the second apparatus via the first wireless technology, a second wireless technology, or a combination of both the first and second wireless technologies, while the first and second apparatuses are still in proximity; and to communicate second information with the second apparatus via the second wireless technology.

Certain aspects of the present disclosure provide a wireless device. The wireless device generally includes at least one antenna and a processing system. The processing system is generally configured to perform an association with an apparatus via a first wireless technology, wherein the first wireless technology requires proximity between the wireless device and the apparatus; to communicate, via the at least one antenna, first information with the apparatus via the first wireless technology, a second wireless technology, or a combination of both the first and second wireless technologies, while the wireless device and the apparatus are still in proximity; and to communicate, via the at least one antenna, second information with the apparatus via the second wireless technology.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

AN EXAMPLE COMMUNICATION SYSTEM

Figure 1:
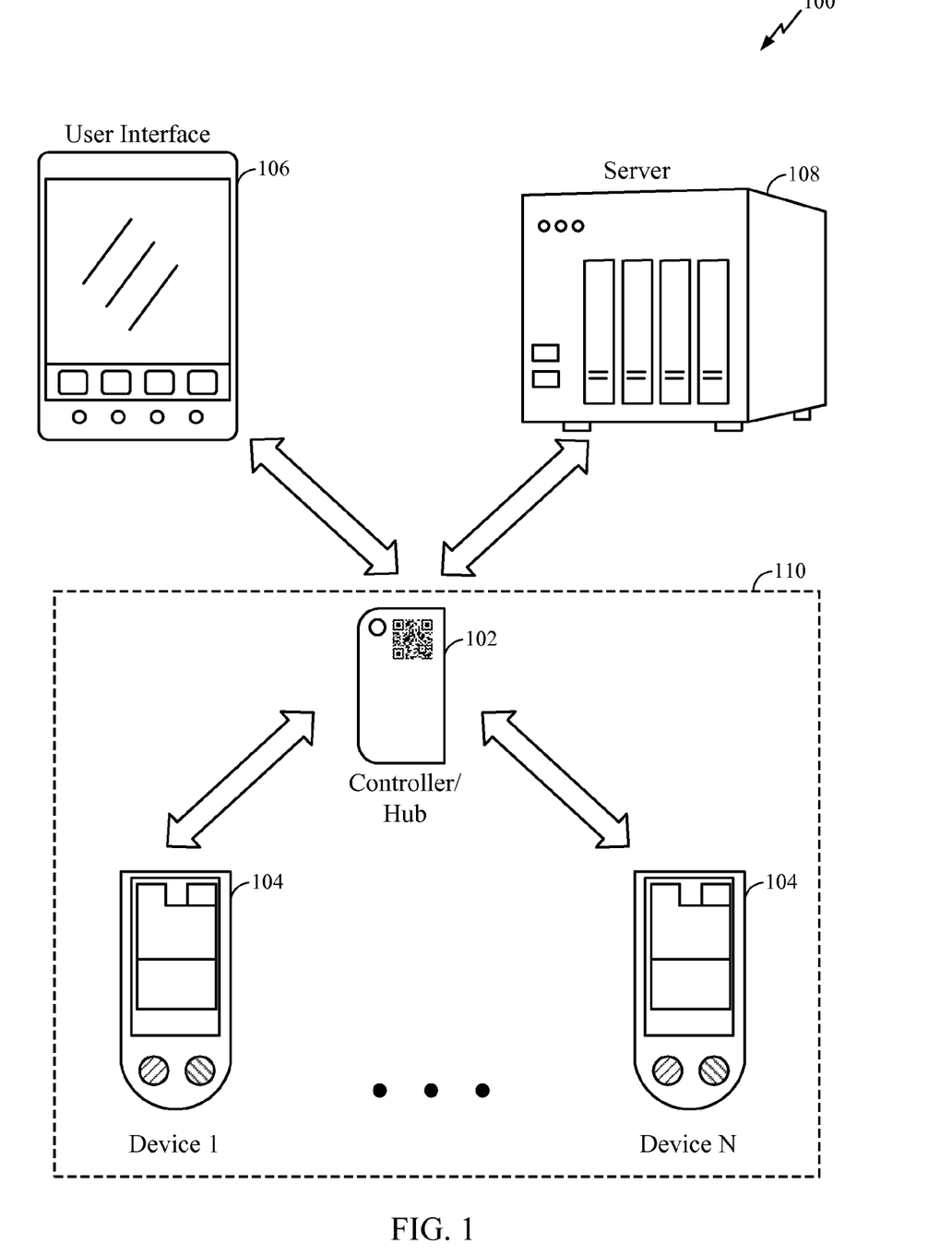
FIG. 1 illustrates a diagram of an example communications network in accordance with certain aspects of the present disclosure.

FIG. 1 illustrates an example distributed communication system 100 with a controller/hub 102 and one or more wireless devices 104. The controller/hub 102 may communicate with the wireless devices 104 via one or more wireless channels using one or more antennas and/or via one or more wired connections. The controller/hub 102 may function similar to an access point (AP) or a Wi-Fi hotspot in an IEEE 802.11 network.

The communication system 100 may be used in a healthcare environment, such as a hospital, clinic, hospice, or home. In such cases, the wireless devices 104 may include any of various suitable wireless medical devices, such as an infusion pump, a blood pressure monitor, a pulse oximeter, an electrocardiograph (ECG), and the like. The controller/hub 102 may be associated with a single patient, and the controller/hub 102 and the wireless devices associated therewith may form an in-room network 110. The in-room network 110 may function similar to a local area network (LAN) or a home network. Certain wireless devices 104 may be worn by the patient (e.g., a finger-worn or wrist-worn unit); inserted or implanted into the patient's body; or attached to or embedded in the patient's bed, gurney, clothing, or other devices that would generally stay physically close to the patient (e.g., a walker, cane, watch, or glasses).

Wireless communication between the controller/hub 102 and a wireless device 104 may use any of various suitable wireless technologies, such as near field communication (NFC), Bluetooth, Bluetooth Low Energy (BTLE), Wi-Fi in accordance with the IEEE 802.11 standard, Zigbee, ANT/ANT+, Toumaz Healthcare Ltd.'s Sensium™ platform for developing body area networks (BANs), Medical Implant Communication Service (MICS), and the like. The wireless communication may also occur via infrared (IR), bar code scanning, or other optical technologies.

A user interface 106 may provide an interface for a user (e.g., a doctor, a nurse, or the patient himself) to communicate with the controller/hub 102. The user interface 106 may comprise a networked device, such as a tablet (as shown), a smart phone, a cellular phone, a laptop, or dedicated electronic hardware. The user interface 106 may be connected with the controller/hub 102, a healthcare facility intranet (e.g., a hospital intranet), or the wireless device 104 directly via physical wires, wirelessly, or both. The connection between the user interface 106 and the controller/hub 102 or the wireless device 104 may be part of the in-room network 110.

A server 108 may provide an interface between the controller/hub 102 and a healthcare facility intranet. As part of the healthcare information system (HIS), the server 108 may store and provide access to electronic medical records (EMRs) of the patients and may provide the intelligence for checking therapies against patient allergies, preventing conflicting medications, etc. For certain aspects, the controller/hub 102 may provide the only interface between the in-room network 110 and the facility intranet. The controller/hub 102 may be connected with the facility intranet directly via a wired technology (e.g., Ethernet), indirectly via a wireless router connected to the server 108 via a wired technology, or indirectly via a public or private wired, wireless, or hybrid network technology.

One example scenario of the interactions between the various apparatus in the communication system 100 in a healthcare environment involves drug delivery to a patient. First, an infusion pump (e.g., a wireless device 104) may scan the patient's identification (ID), which may be contained in a bar code wristband worn by the patient. Then NFC may be used for out-of-band pairing between the controller/hub 102 and the pump. The pump may inform the controller/hub 102 of the patient's ID. Based on this, the controller/hub 102 may query the HIS/EMR for the patient's treatment information. Once this information is received, the controller/hub 102 may configure the pump (i.e., may transmit configuration information to the pump) for a particular intravenous (IV) therapy treatment. The configuration information may include the set of solution and medication, the solution's density, the flow rate, the total volume to infuse, and an interval (in an intermittent flow pattern) for an intravenous therapy the patient is prescribed to receive. The user interface 106 may prompt the caregiver to confirm the treatment, and once the caregiver confirms, the caregiver may scan a bar code, a quick response (QR) code, or a radio frequency identification (RFID), for example, on an IV solution bag before or after the caregiver connects the bag with the pump. The controller/hub 102 may signal the infusion pump to begin the treatment, perhaps at the command of the caregiver. Data from the pump may be transmitted to the controller/hub 102, and particular received data may be transmitted to the HIS via the healthcare facility intranet or other wireless or wired links.

Figure 2:
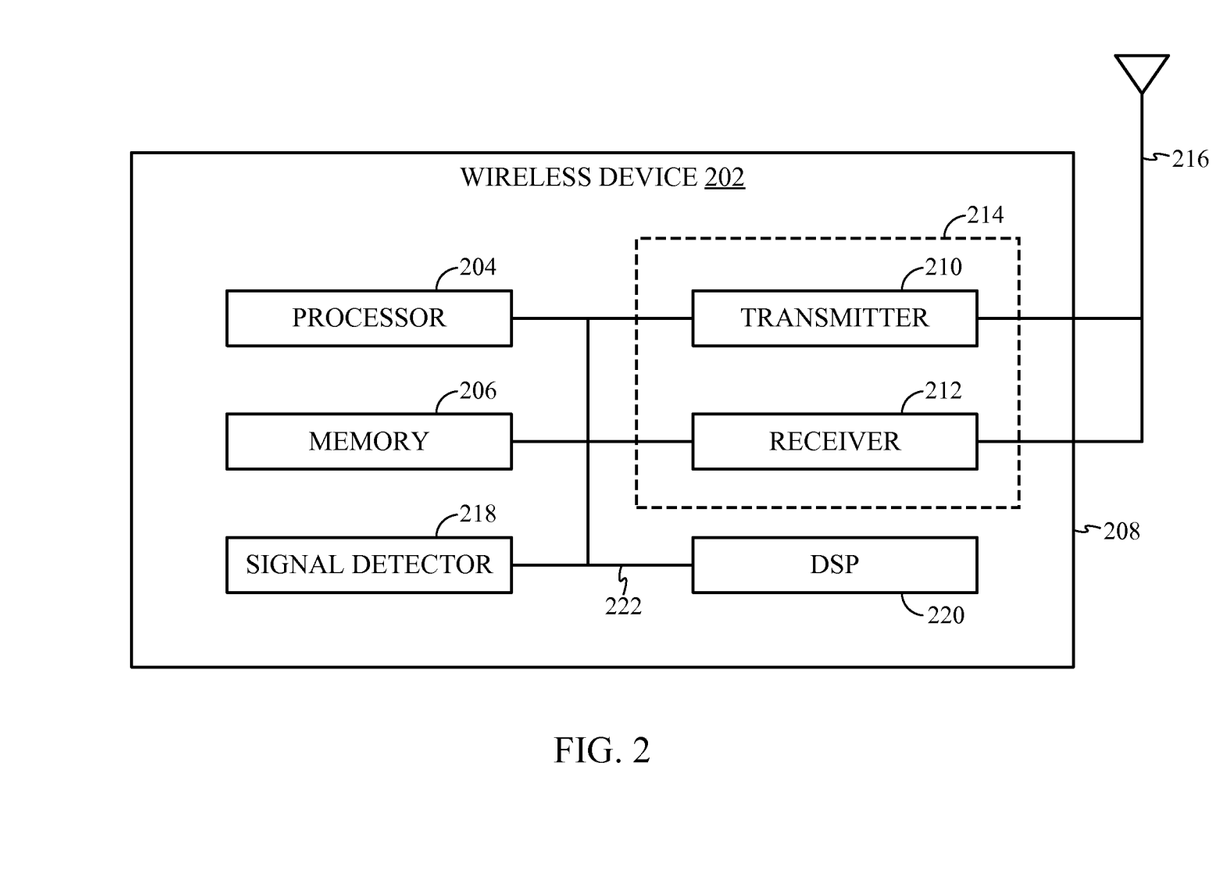
FIG. 2 illustrates a block diagram of an example wireless device in accordance with certain aspects of the present disclosure.

FIG. 2 illustrates various components that may be utilized in a wireless device 202. The wireless device 202 is an example of a device that may be configured to implement the various methods described herein. The wireless device 202 may be a controller/hub 102 or a wireless device 104, as described above with respect to FIG. 1.

The wireless device 202 may include a processor 204 which controls operation of the wireless device 202. The processor 204 may also be referred to as a central processing unit (CPU). Memory 206, which may include both read-only memory (ROM) and random access memory (RAM), provides instructions and data to the processor 204. A portion of the memory 206 may also include non-volatile random access memory (NVRAM). The processor 204 typically performs logical and arithmetic operations based on program instructions stored within the memory 206. The instructions in the memory 206 may be executable to implement the methods described herein.

The wireless device 202 may also include a housing 208 that may include a transmitter 210 and a receiver 212 to allow transmission and reception of data between the wireless device 202 and a remote location. The transmitter 210 and receiver 212 may be combined into a transceiver 214. An antenna 216 may be attached to the housing 208 and electrically coupled to the transceiver 214. The wireless device 202 may also include (not shown) multiple transmitters, multiple receivers, multiple transceivers, and/or multiple antennas.

The wireless device 202 may also include a signal detector 218 that may be used in an effort to detect and quantify the level of signals received by the transceiver 214. The signal detector 218 may detect such signals as total energy, pilot energy from pilot subcarriers or signal energy from the preamble symbol, power spectral density, and other signals. The wireless device 202 may also include a digital signal processor (DSP) 220 for use in processing signals.

The various components of the wireless device 202 may be coupled together by a bus system 222, which may include a power bus, a control signal bus, and a status signal bus in addition to a data bus.

EXAMPLE DISTRIBUTED CONTROL OF MEDICAL DEVICES

Current practice is for most medical devices to have their own built-in display, controls, etc. for maintaining their configuration and displaying any data that the devices collect. Providing a centralized device that can serve as a user interface, display, and controller for medical equipment allows the medical equipment to decrease in size and cost for the same display, control, and communication capabilities or to increase these capabilities without adding to the complexity or cost of the individual equipment. In addition, the opportunities for automated configuration, as well as for automated recording of data into electronic medical records, offer the promise of improved tracking of patient data and reduced errors in medication. The patient's equipment then becomes a distributed system with a common controller. The value of such a system increases greatly when the links between devices are wireless. However, such links are subject to interruption (e.g., via interference). Appropriate care may most likely be taken to ensure that interruptions in communication do not degrade the quality of care. Furthermore, one controller may be asked to control a number of different devices, thereby aggravating the effects of any unreliable communication links.

Certain aspects of the present disclosure are based on the realization that some data is more important (i.e., more critical) than others. For example, it may be desirable to transfer configuration data to an infusion pump correctly, without errors in the transmission. Once treatment has been initiated, treatment progress, faults, etc. may be sent repeatedly (e.g., periodically) in a manner, such that missed data packets have little impact on the system. Therefore, interactions within the distributed system may be designed such that critical information is transmitted while the devices 104 are being associated with the controller/hub 102, or shortly thereafter. For certain aspects, this may be accomplished by transmitting some configuration data (e.g., a Uniform Resource Locator (URL) of the controller) via Bluetooth pairing, etc. The association and/or configuration data may be transmitted via a wireless technology that relies on proximity of the devices, such as near field communication (NFC) (e.g., using radio frequency identification (RFID)), a quick response (QR) code scan, a bar code scan, or a system that determines presence through proximity detection or received signal strength. This may guarantee a sufficient link budget for the critical data, thereby reducing communication errors.

For certain aspects, the controller/hub 102 and/or the wireless device 104 may indicate whether the association and/or configuration data is successfully received (e.g., whether the out-of-band pairing between the controller/hub 102 and the device 104 was completed). This indication may include an auditory signal (e.g., a tone, chirp, chime, beep, jingle, tune, synthesized voice, or other audible sound), a tactile sensation (e.g., a vibration), a visual indication (e.g., a light or a displayed message), or any combination thereof.

To manage multiple devices in an efficient fashion once the devices 104 are operating, these devices may repeatedly (e.g., continually, periodically, or intermittently) transmit a beacon that the controller/hub 102 can monitor. The beacon may also be known as a "heartbeat" or a keep-alive message. For certain aspects, the beacon may be randomized in time, frequency, and/or code space and spaced apart so that beacons from multiple devices have a low probability of collision. The beacon may have a small payload to increase availability of the channel for other devices. Such a payload may include a small amount of performance data, plus a code indicating whether a fault (i.e., an error) or other event has occurred that would call for interactive communications between the controller/hub 102 and the device 104. The controller/hub 102 may monitor the beacons to track the progress of the various ongoing treatments or operations, as well as to determine that the various devices 104 are still in range and operating. When one or more devices 104 begin indicating faulty operation, the controller/hub 102 may prioritize among devices in an effort to provide the best care for the patient.

Providing communications in this manner reduces the communication burden on the controller/hub 102 and enables robust operation of many devices 104 with a single controller/hub.

Figure 3:
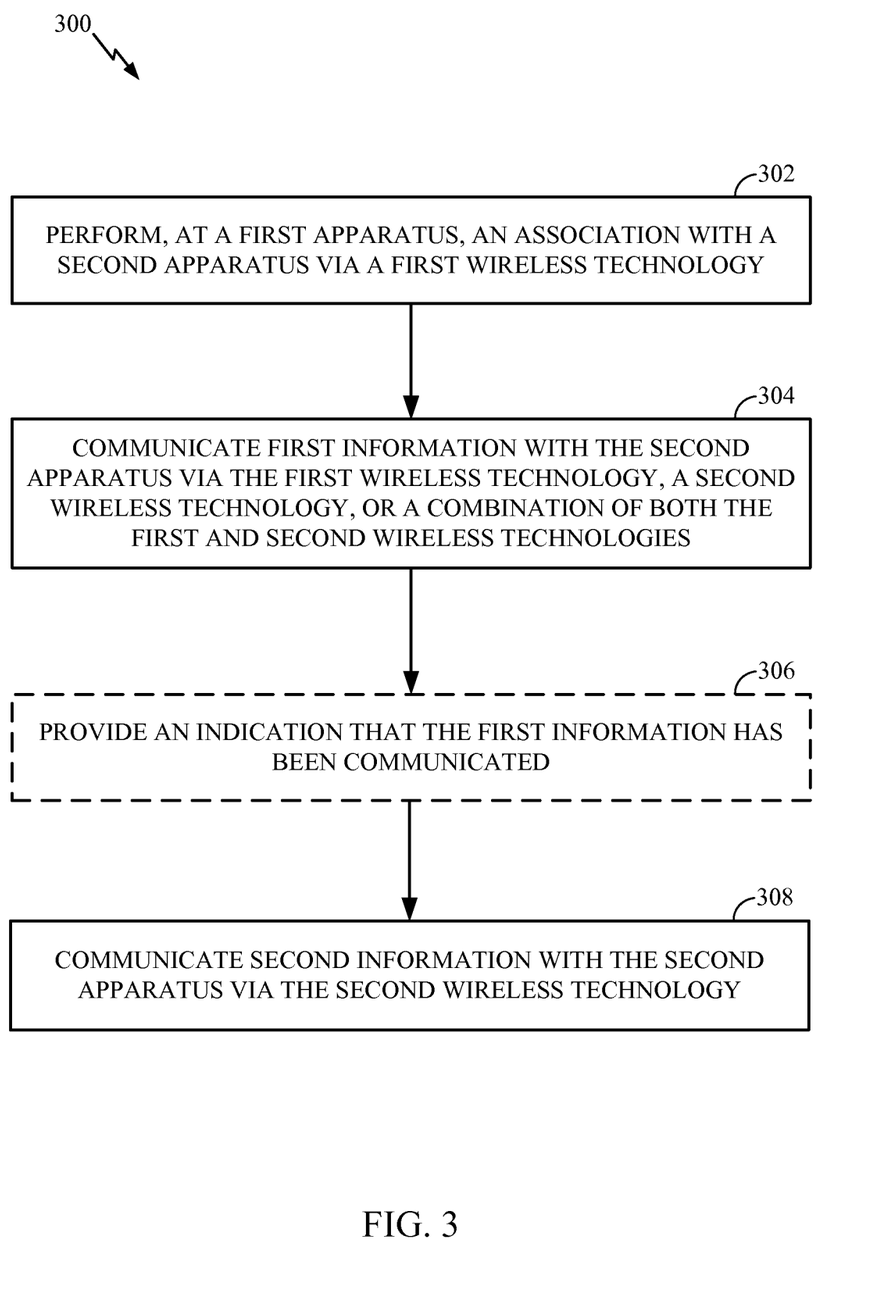
FIG. 3 illustrates example operations for communicating relatively more or less critical information between devices using wireless technologies that are less or more susceptible to interference, respectively, from the perspective of a controller/hub or a wireless device, in accordance with certain aspects of the present disclosure.

FIG. 3 illustrates example operations 300 for communicating relatively more or less critical information between devices using wireless technologies that are less or more susceptible to interference, respectively, in accordance with certain aspects of the present disclosure. The operations 300 may be performed by a first apparatus, such as a controller/hub 102 or a wireless device 104.

At 302, the first apparatus may perform an association with a second apparatus via a first wireless technology. If the first apparatus is a controller/hub 102, then the second apparatus may comprise a wireless device 104, such as any of various suitable wireless medical devices (e.g., an infusion pump, a blood pressure monitor, a pulse oximeter, an ECG, and the like). The first wireless technology may require proximity between the first and second apparatuses. For an example of proximity, the first information may be communicated at 302 if a distance between the first and second apparatuses is sufficiently short to provide a high level of assurance that the first apparatus is communicating with the second apparatus and not a different apparatus. In other words, the first information may be communicated if a distance between the first apparatus and the second apparatus enables the first apparatus to communicate only with the second apparatus. For NFC, for example, proximity may require a distance of less than or equal to about five centimeters (5 cm). Other wireless technologies may have different requirements for proximity.

At 304, the first apparatus may communicate first information with the second apparatus via the first wireless technology, a second wireless technology, or a combination of both the first and second wireless technologies. This communication may occur while the first and second apparatuses are still in proximity. As used herein, the term "communication" may include transmission, reception, or both. The second wireless technology may not require proximity. The first information may comprise configuration information.

At 306, the first apparatus may provide an indication that the first information has been communicated. The indication may include any of various suitable signals, such as an auditory signal, a tactile sensation, a visual indication, or any combination thereof, as described above.

At 308, the first apparatus may communicate second information with the second apparatus via the second wireless technology. The first information may be relatively more critical to communication between the first and second apparatus than the second information. Furthermore, the first wireless technology may be less susceptible to interference than the second wireless technology (e.g., due to proximity). For example, the first technology may comprise at least one of NFC, RFID, a QR code scan, a bar code scan, or a technology based on proximity detection or received signal strength. For certain aspects, the first apparatus may communicate the first information only if a distance between the first apparatus and the second apparatus is less than or equal to about one meter (1 m). The second technology may comprise Bluetooth or BTLE, for example, which may have a range up to about 10 m.

The second information may comprise a beacon message (e.g., a heartbeat or keep-alive message) and may indicate that the second apparatus is functioning and within range of the first apparatus. The second information may comprise at least one of data from the second apparatus or an indication of whether an event, such as an error, has occurred at the second apparatus. The indication of the event may comprise a fault code. For certain aspects, the second apparatus may determine a parameter, such as an amount of fluid pumped, a heart rate, a blood pressure, a glucose level, and the like. The data from the second apparatus may comprise at least one of an indication of the determined parameter.

According to certain aspects, the second apparatus is an infusion pump. For certain aspects, the first information includes identification information for at least one of patient identification, treatment information (e.g., prescription information) an intravenous (IV) bag associated with the infusion pump, or content of the IV bag.

Figure 3A:
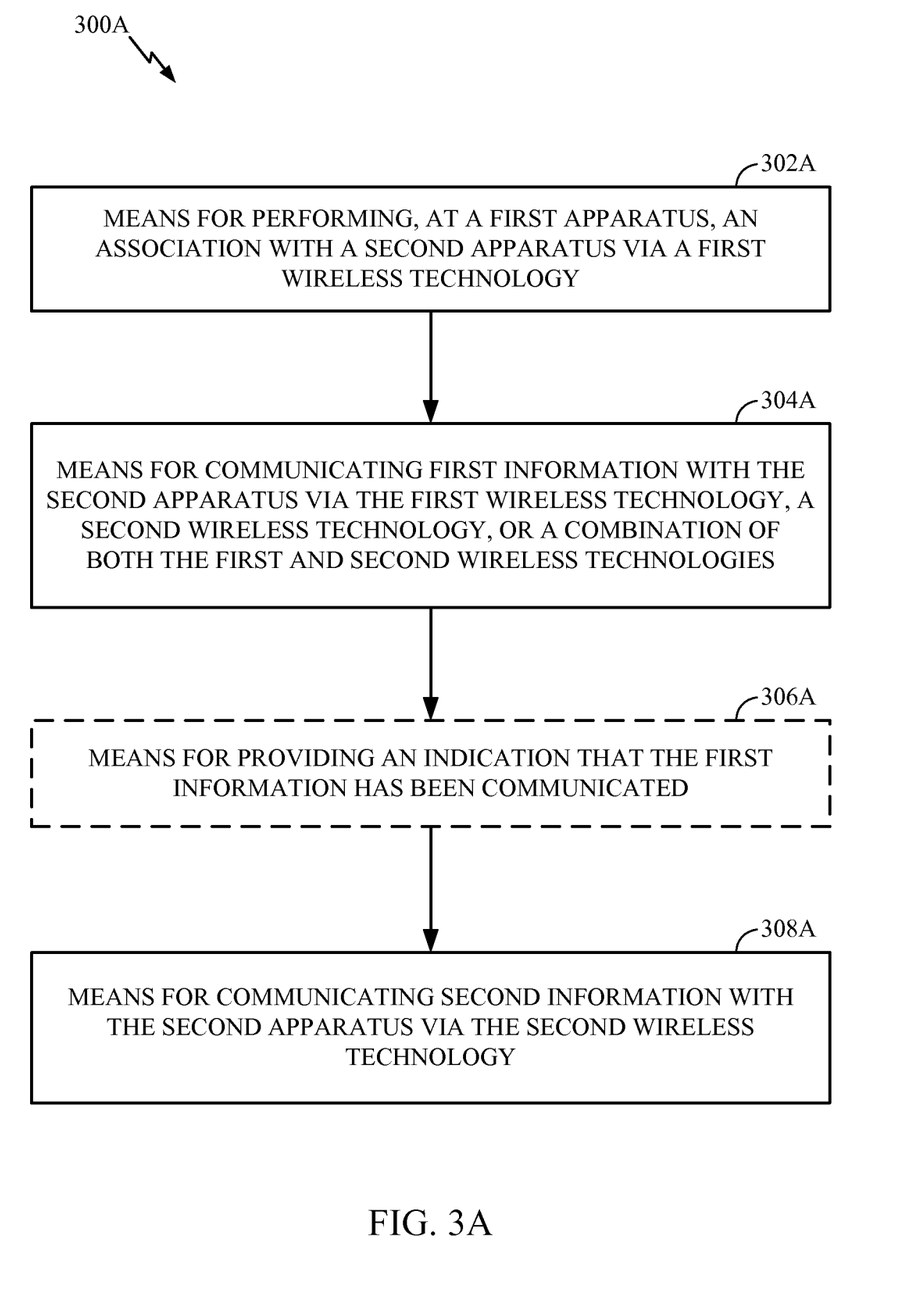
FIG. 3A illustrates example means for performing the operations shown in FIG. 3.

The various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering. For example, operations 300 illustrated in FIG. 3 correspond to means 300A illustrated in FIG. 3A.

For example, means for transmitting may comprise a transmitter, such as the transmitter 210 of the wireless device 202 illustrated in FIG. 2. Means for receiving may comprise a receiver, such as the receiver 212 of the wireless device 202 shown in FIG. 2. Means for performing an association, means for communicating, means for providing an indication, means for determining, and/or means for processing may comprise a processing system, which may include one or more processors, such as processor 204 illustrated in FIG. 2.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory), and the like. Also, "determining" may include resolving, selecting, choosing, establishing, and the like.

As used herein, a phrase referring to "at least one of" a list of items refers to any combination of those items, including single members. As an example, "at least one of a, b, or c" is intended to cover: a, b, c, a-b, a-c, b-c, and a-b-c.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM, and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof If implemented in hardware, an example hardware configuration may comprise a processing system in a wireless node. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement the signal processing functions of the PHY layer. In the case of a user terminal or other wireless node, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processor may be responsible for managing the bus and general processing, including the execution of software stored on the machine-readable media. The processor may be implemented with one or more general-purpose and/or special-purpose processors. Examples include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof The machine-readable media may be embodied in a computer-program product. The computer-program product may comprise packaging materials.

In a hardware implementation, the machine-readable media may be part of the processing system separate from the processor. However, as those skilled in the art will readily appreciate, the machine-readable media, or any portion thereof, may be external to the processing system. By way of example, the machine-readable media may include a transmission line, a carrier wave modulated by data, and/or a computer product separate from the wireless node, all which may be accessed by the processor through the bus interface. Alternatively, or in addition, the machine-readable media, or any portion thereof, may be integrated into the processor, such as the case may be with cache and/or general register files.

The processing system may be configured as a general-purpose processing system with one or more microprocessors providing the processor functionality and external memory providing at least a portion of the machine-readable media, all linked together with other supporting circuitry through an external bus architecture. Alternatively, the processing system may be implemented with an ASIC (Application Specific Integrated Circuit) with the processor, the bus interface, the user interface in the case of an access terminal), supporting circuitry, and at least a portion of the machine-readable media integrated into a single chip, or with one or more FPGAs (Field Programmable Gate Arrays), PLDs (Programmable Logic Devices), controllers, state machines, gated logic, discrete hardware components, or any other suitable circuitry, or any combination of circuits that can perform the various functionality described throughout this disclosure. Those skilled in the art will recognize how best to implement the described functionality for the processing system depending on the particular application and the overall design constraints imposed on the overall system.

The machine-readable media may comprise a number of software modules. The software modules include instructions that, when executed by the processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module below, it will be understood that such functionality is implemented by the processor when executing instructions from that software module.

If implemented in software, the functions may be stored or transmitted over as one or more instructions or code on a computer-readable medium. Computer-readable media include both computer storage media and communication media including any medium that facilitates transfer of a computer program from one place to another. A storage medium may be any available medium that can be accessed by a computer. By way of example, and not limitation, such computer-readable media can comprise RAM, ROM, EEPROM, CD-ROM, or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes, and variations may be made in the arrangement, operation, and details of the methods and apparatus described above without departing from the scope of the claims.

The invention claimed is:

1. A first apparatus for wireless communications, comprising:
a processing system configured to:
perform an association with a second apparatus comprising a medical device via a first wireless technology, wherein the first wireless technology requires proximity between the first and second apparatuses;
communicate first information with the second apparatus via the first wireless technology, while the first and second apparatuses are still in proximity, wherein the first information comprises configuration information to configure the medical device to, at least one of, treat or monitor a patient; and
communicate second information with the second apparatus via the second wireless technology, wherein the second wireless technology is different from the first wireless technology, and wherein the second information comprises at least one of the following: an indication that the second apparatus is functioning and within range of the first apparatus, an indication of whether an event has occurred that would call for interactive communication, or an indication of whether an error has occurred at the second apparatus.

2. The first apparatus of claim 1, wherein the processing system is further configured to provide an indication that the first information had been communicated.

3. The first apparatus of claim 1, wherein the first information is communicated if a distance between the first apparatus and the second apparatus is less than or equal to about 1 meter.

4. The first apparatus of claim 1, wherein the first information is communicated if a distance between the first apparatus and the second apparatus enables the first apparatus to communicate only with the second apparatus.

5. The first apparatus of claim 1, wherein the first wireless technology comprises one of near field communication (NFC), radio frequency identification (RFID), a quick response (QR) code scan, or a bar code scan.

6. The first apparatus of claim 1, wherein the second information indicates that the second apparatus is functioning and within range of the first apparatus.

7. The first apparatus of claim 1, wherein the second information indicates whether an event has occurred that would call for interactive communication.

8. The first apparatus of claim 1, wherein the second wireless technology comprises one of Bluetooth or Bluetooth Low Energy (BTLE).

9. The first apparatus of claim 1, wherein the second apparatus comprises an infusion pump.

10. The first apparatus of claim 9, wherein the first information comprises identification information for at least one of patient identification, treatment information, an intravenous (IV) bag associated with the infusion pump, or content of the IV bag.

11. The first apparatus of claim 1, wherein the second information indicates whether an error has occurred at the apparatus.

12. The first apparatus of claim 1, wherein the configuration information comprises medical information that instructs the medical device to implement a particular medical treatment for the patient.

13. The first apparatus of claim 1, wherein the configuration information comprises information regarding a medication flow rate, a medication volume, or a medication interval for treatment of the patient by the medical device.

14. A method for wireless communications by a first apparatus, comprising:
performing an association with a second apparatus comprising a medical device via a first wireless technology, wherein the first wireless technology requires proximity between the first and second apparatuses;
communicating first information with the second apparatus via the first wireless technology, while the first and second apparatuses are still in proximity, wherein the first information comprises configuration information to configure the medical device to, at least one of, treat or monitor a patient; and
communicating second information with the second apparatus via the second wireless technology, wherein the second wireless technology is different from the first wireless technology, and wherein the second information comprises at least one of the following: an indication that the second apparatus is functioning and within range of the first apparatus, an indication of whether an event has occurred that would call for interactive communication, or an indication of whether an error has occurred at the second apparatus.

15. The method of claim 14, further comprising providing an indication that the first information had been communicated.

16. The method of claim 14, wherein the first information is communicated if a distance between the first apparatus and the second apparatus is less than or equal to about 1 meter.

17. The method of claim 14, wherein the first information is communicated if a distance between the first apparatus and the second apparatus enables the first apparatus to communicate only with the second apparatus.

18. The method of claim 14, wherein the first wireless technology comprises one of near field communication (NFC), radio frequency identification (RFID), a quick response (QR) code scan, or a bar code scan.

19. The method of claim 14, wherein the second information indicates that the second apparatus is functioning and within range of the first apparatus.

20. The method of claim 14, wherein the second information indicates whether an event has occurred that would call for interactive communication.

21. The method of claim 14, wherein the second wireless technology comprises one of Bluetooth or Bluetooth Low Energy (BTLE).

22. The method of claim 14, wherein the second apparatus comprises an infusion pump.

23. The method of claim 22, wherein the first information comprises identification information for at least one of patient identification, treatment information, an intravenous (IV) bag associated with the infusion pump, or content of the IV bag.

24. The method of claim 14, wherein the second information indicates whether an error has occurred at the apparatus.

25. A first apparatus for wireless communications, comprising:
means for performing an association with a second apparatus comprising a medical device via a first wireless technology, wherein the first wireless technology requires proximity between the first and second apparatuses;
means for communicating first information with the second apparatus via the first wireless technology, while the first and second apparatuses are still in proximity, wherein the first information comprises configuration information to configure the medical device to, at least one of, treat or monitor a patient; and means for communicating second information with the second apparatus via the second wireless technology, wherein the second wireless technology is different from the first wireless technology, and wherein the second information comprises at least one of the following: an indication that the second apparatus is functioning and within range of the first apparatus, an indication of whether an event has occurred that would call for interactive communication, or an indication of whether an error has occurred at the second apparatus.

26. The first apparatus of claim 25, further comprising means for providing an indication that the first information had been communicated.

27. The first apparatus of claim 25, wherein the means for communicating the first information is configured to communicate the first information if a distance between the first apparatus and the second apparatus is less than or equal to about 1 meter.

28. The first apparatus of claim 25, wherein the means for communicating the first information is configured to communicate the first information if a distance between the first apparatus and the second apparatus enables the first apparatus to communicate only with the second apparatus.

29. The first apparatus of claim 25, wherein the first wireless technology comprises one of near field communication (NFC), radio frequency identification (RFID), a quick response (QR) code scan, or a bar code scan.

30. The first apparatus of claim 25, wherein the second information indicates that the second apparatus is functioning and within range of the first apparatus.

31. The first apparatus of claim 25, wherein the second information indicates whether an event has occurred that would call for interactive.

32. The first apparatus of claim 25, wherein the second wireless technology comprises one of Bluetooth or Bluetooth Low Energy (BTLE).

33. The first apparatus of claim 25, wherein the second apparatus comprises an infusion pump.

34. The first apparatus of claim 33, wherein the first information comprises identification information for at least one of patient identification, treatment information, an intravenous (IV) bag associated with the infusion pump, or content of the IV bag.

35. The first apparatus of claim 25, wherein the second information indicates whether an error has occurred at the apparatus.

36. A computer-program product for wireless communications by a first apparatus, comprising a non-transitory computer-readable medium having instructions executable to:

perform an association with a second apparatus comprising a medical device via a first wireless technology, wherein the first wireless technology requires proximity between the first and second apparatuses;

communicate first information with the second apparatus via the first wireless technology, while the first and second apparatuses are still in proximity, wherein the first information comprises configuration information to configure the medical device to, at least one of, treat or monitor a patient; and communicate second information with the second apparatus via the second wireless technology, wherein the second wireless technology is different from the first wireless technology, and wherein the second information comprises at least one of the following: an indication that the second apparatus is functioning and within range of the first apparatus, an indication of whether an event has occurred that would call for interactive communication, or an indication of whether an error has occurred at the second apparatus.

37. A wireless device, comprising:

at least one antenna; and a processing system configured to:

perform an association with an apparatus comprising a medical device via a first wireless technology, wherein the first wireless technology requires proximity between the wireless device and the apparatus;

communicate, via the at least one antenna, first information with the apparatus via the first wireless technology, while the wireless device and the apparatus are still in proximity, wherein the first information comprises configuration information to configure the medical device to, at least one of, treat or monitor a patient; and communicate, via the at least one antenna, second information with the apparatus via the second wireless technology, wherein the second wireless technology is different from the first wireless technology, and wherein the second information comprises at least one of the following: an indication that the apparatus is functioning and within range of the first apparatus, an indication of whether an event has occurred that would call for interactive communication, or an indication of whether an error has occurred at the apparatus.

* * * * *